United States Patent [19]

Gordon

[11] Patent Number: 4,729,239

[45] Date of Patent: Mar. 8, 1988

[54] VIBRATION TESTER FOR BALL BEARINGS AND ASSOCIATED DEVICES

[75] Inventor: Keith M. Gordon, Munsonville, N.H.

[73] Assignee: MPB Corporation, Keene, N.H.

[21] Appl. No.: 945,262

[22] Filed: Dec. 19, 1986

[51] Int. Cl.[4] ............................................. G01M 13/04
[52] U.S. Cl. .......................................... 73/593; 73/660
[58] Field of Search ........................... 73/593, 660, 666; 340/682

[56] References Cited

U.S. PATENT DOCUMENTS

| 2,468,648 | 4/1949 | Abbott et al. | 73/593 |
| 3,677,072 | 7/1972 | Weichbrodt et al. | 73/593 |

FOREIGN PATENT DOCUMENTS

| 0039010 | 3/1980 | Japan | 73/593 |

Primary Examiner—Stewart J. Levy
Assistant Examiner—Lawrence Fess

[57] ABSTRACT

The invention is directed to a miniature ball bearing tester which detects vibrations therefrom when such a bearing is rotated by a rotor. The device includes a base upon which are supported reeds. The reeds support an upper housing tooling which includes a bearing support for mounting a bearing thereon for rotation. A rotor is attachable to a bearing mounted on the upper tooling. The rotor is then driven to rotate the bearing and upon a defect being detected, the reeds are as a result forced to move in a direction radial with respect to the axial direction of the bearing. An accelerometer picks up the movement and the signal therefrom is then band pass filtered, integrated to obtain a velocity measurement and output by, for example, a speaker to detect any frequencies resulting from a flaw in the miniature bearing.

12 Claims, 4 Drawing Figures

VIBRATION TESTER FOR BALL BEARINGS AND ASSOCIATED DEVICES

BACKGROUND OF THE INVENTION

This invention is directed to a vibration tester for ball bearings and associated devices which permits rapid screening of the units by manufacturers or users. More specifically, the invention is especially useful in testing miniature ball bearings (defined, for the purpose of this invention, as those bearings having OD less than 40 mm, but not limited to this size range).

A basic device, known as an Anderometer is used for testing and classifying imperfections in ball and roller bearings and is disclosed in U.S. Pat. No. 2,468,648. In accordance with this device, the radial velocity of the outer ring of a bearing is measured, with the bearings' inner ring spun on a spindle. This device has been successfully employed for measuring and detecting flaws in large bearings, however, it is too insensitive to measure imperfections in miniature bearings.

U.S. Pat. No. 3,745,815 discloses a device similar to the above-discussed Anderometer which provides a device wherein a bearing is spun on a spndle and a pick off measures the radial motion of the outer race. This patent disclosure is primarily concerned with the processing of the signal once it leaves the pick off. The disclosed circuitry measures in a high frequency range in response to the presence of pulse trains in the signal and not the signal itself.

Still further, a device disclosed in U.S. Pat. No. 3,023,604 having an inventor in common with the inventorship of this invention discloses a device called a VANT (Vibration and Noise Tester). This device measures axial velocity but its major problem is that it is difficult to calibrate and resonance is detected in the frequency window within which measurements are taken. Thus, results are interferred with as a result of resonance.

U.S. Pat. Nos. 1,992,453, 2,364,229, 2,796,759, 3,095,730 and 3,332,277 are illustrative of other types of devices used for measuring bearings. However, as in the case with the above-specifically disclosed devices, all of these devices suffer in that they are not readily adaptable for use in testing miniature bearings due to lack of sensitivity and thus are primarily limited to the testing of large massive bearings.

SUMMARY OF THE INVENTION

In accordance with the invention, there is provided a device for testing ball bearings, and especially miniature ball bearings and associated devices to detect flaws therein by detecting vibrations therefrom when in rotated operation. As can be readily appreciated, the smaller the components being tested the smaller the relative flaws and thus, the more difficult to detect.

Thus, in accordance with the invention the device for testing ball bearings and associated devices to detect flaws therein by detecting vibrations therefrom when in operation comprises a ba.:c. A reed support is attached to the base and extends upwardly therefrom. The reed support is for supporting an upper housing tooling. An upper housing tooling is mounted on the reed support with the upper housing tooling having means for supporting a bearing thereon for rotational operation. The reed support, relative to the base, is flexible in a direction radial to the axis of rotation of a bearing mounted on the upper housing tooling. A drive mechanism serves to rotationally drive a bearing mounted on the upper housing tooling. A reed motion detecting arrangement is connected to the reed support for detecting movement of the reed support in response to a bearing on the upper housing tooling be rotated. The movement detected is indicative of a defect in the bearing.

In a more specific aspect, the invention further comprises velocity detecting means for detecting the velocity of rotation at which a bearing is being rotated. The drive mechanism comprises a rotor body connectable to a bearing which is configured for being driven in rotation by a pressurized air supply impinging thereon. With respect to the velocity detecting means, it preferably comprises a combination of a photocell and a infrared LED positioned to have the radiation from the LED transmitted to the photocell and interrupted by predetermined portions of the rotor body upon rotation thereof to determine the speed of rotation of the rotor body as a function of photocell output.

As to the detecting mechanism for detecting motion of the reed support, it preferably comprises an accelerometer connected to the reed support to detect flexing thereof in a radial direction relative to a rotating bearing. The reed support itself is selected to have a length and thickness such that the resonant frequency of the reed support with the upper housing tooling mounted thereon is at a value well below the lowest frequency measured by the accelerometer, which lowest frequency measured is indicative of a flaw in a bearing being tested.

In a still more preferred aspect, the accelerometer is connected to output electronics. The output electronics preferably includes an accelerometer preamplifier for amplifying, filtering and integrating the output from the accelerometer to obtain a velocity signal indicative of movement of the reed support. An RMS meter serves to receive the velocity signal and determines the RMS value thereof. An amplifier serves to amplify this resultant signal from the RMS meter and an output device outputs a human perceptible representation of the signal. In still more preferred aspect, the output device can be a speaker, a set of headphones, an oscilloscope or a real time analyzer. In a still more specific aspect of the electronics, the invention also includes a band pass filter of the type which passes frequencies which are above 50 Hertz, and wherein the accelerometer is of the type which is capable of measuring frequencies only as low as about 30 Hertz. The band pass filter is arranged subsequent to the accelerometer, preferably as part of the accelerometer preamplifier circuitry prior to amplification and integration of signal from the accelerometer.

BRIEF DESCRIPTION OF THE DRAWINGS

Having briefly discussed the invention, the same will become better understood from the following detailed discussion, taken in conjunction with the attached drawings wherein.

DETAILED DISCUSSION OF THE INVENTION

Figure 1:
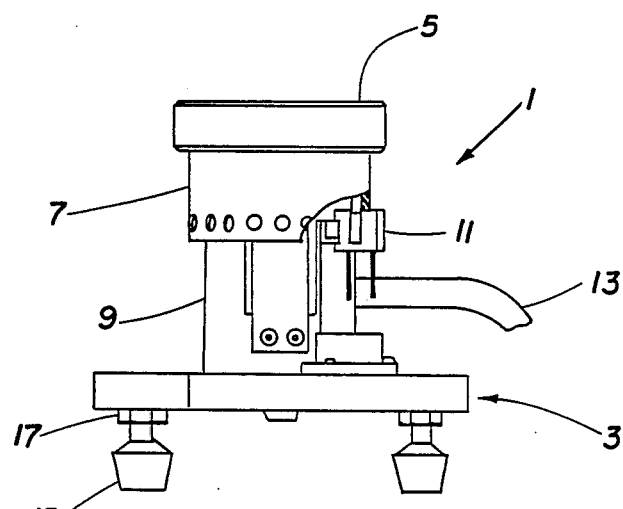
FIG. 1 is a partial cross-sectional view of the device in accordance with the invention.

The device in accordance with the invention is generally shown in FIGS. 1–4. More specifically, in FIG. 1 there is shown a miniature bearing tester 1 which is constructed for allowing measurement of radial vibration velocity of a miniature bearing spinning under an axial load, i.e., a free rotor 5 as shown in FIG. 1.

Figure 3:
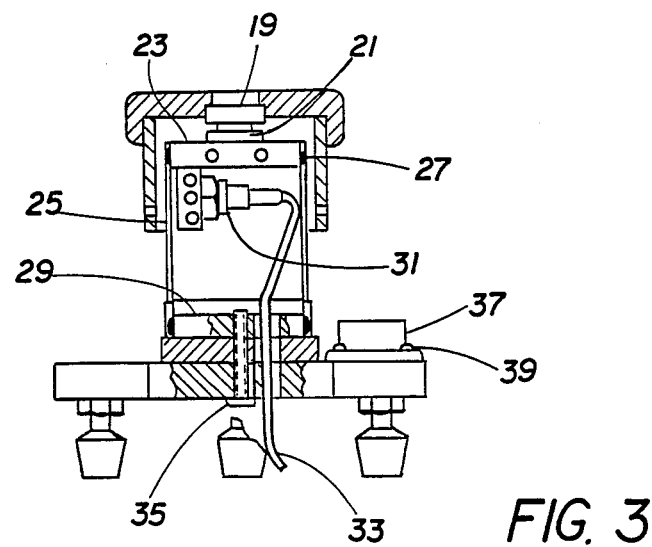
FIG. 3 is a full side-sectional view of the device in accordance with the invention.

As more specifically shown in FIG. 3, the free rotor 5 is mounted attached to a bearing 19 which has its inner, i.e., stationary race mounted on race tooling 21 which is mounted on tooling support 23. The tooling support 23 is mounted on and attached to reed members 25 by means of a cap screw 27 at each end. The reeds 25 are, as previously noted, tuned to be soft in the radial direction relative to the axis of the bearing. The reeds 25 are typically made of thin spring steel of, preferably, ten thousands of an inch. The length and thickness of the reeds 25 is selected such that the resonant frequency of the tooling support 23 is well below the lowest frequency measured by a pick up mechanism which will be discussed hereinafter.

Figure 2:
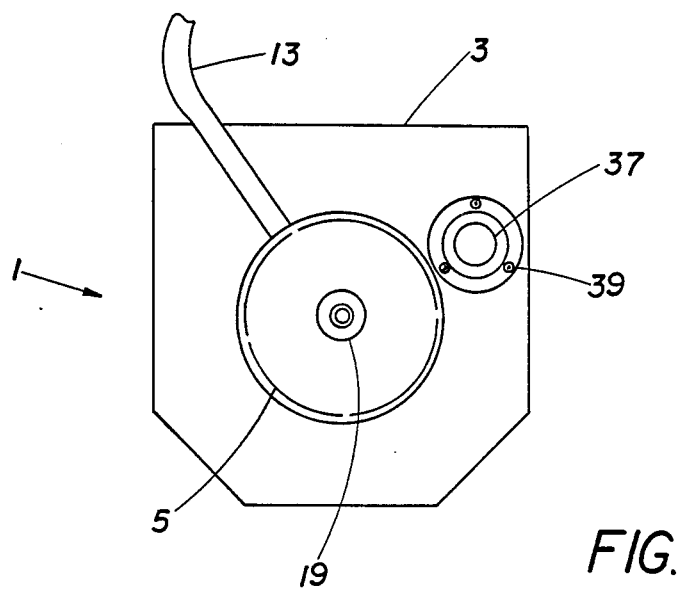
FIG. 2 is a top plan view of the device in accordance with the invention.

As also shown in FIGS. 1 and 2, on the bearing 19 is mounted a rotor 5 having a rotor skirt 7. The bearing 19 is thus driven in rotation by means of an air supply hose 13 which impinges on predetermined portions of the skirt 7 of the rotor 5. This causes the rotor 5 to be driven in rotation. The speed of rotation of the rotor 5 can be measured by means of an infrared LED and photocell pick-up 11 which, as can be seen, comes on and off in accordance with repetitive interruption by means of holes in the skirt 7 which pass therebetween. In this manner, speed of rotation of rotor 5 can be measured and adjusted by variations in the air flow through air hose 13. The skirt 7 overlaps a body 9 which surrounds and encloses the reed assembly within the body 9.

As further shown in FIG. 1, the entire assembly is mounted on a base 3 which includes adjustable legs 15 which are adjustable by means of adjusting nuts 17.

As more specifically shown in FIG. 3, in order to measure any radial vibration caused by imperfections in the bearing 19 upon rotation thereof, an accelerometer 31 is attached to the tooling support 23 and signals generated thereby are transmitted by means of a cable 33 to the pick up electronics. Holding the assembly together is a reed support 29 which is held to the base 3 by means of bolt 35. As further shown in FIG. 2, the accuracy of measurement of the entire assembly depends upon being positioned level so a level 37 is attached to the base 3 by means of screws 39 for this purpose.

Figure 4:
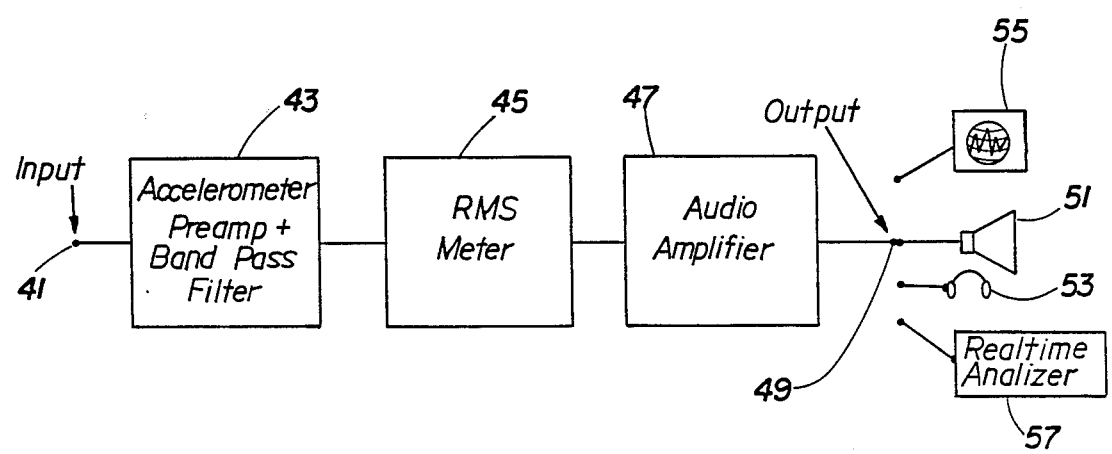
FIG. 4 is a schematic view of the output electronics showing alternative variations which can be employed in conjunction with the device according to the invention.

With respect to the electronics employed to pick up any radial vibrations from the bearing 19, the electronics are straight forward as more clearly shown schematically in FIG. 4. More specifically, the cable 33 is connected to input 41 which connects and transmits signals from the accelerometer 31 to an accelerometer preamplifier and band pass filter 43. The band pass filter is preferably selected such that all frequencies below about 50 Hertz are cut out and the accelerometer 31 itself is such that the lowest frequency measured by it is typically, about 10 Hertz in the case of miniature bearings. Thus, by selecting the reeds 25, as previously discussed, such that the resonant frequency of the upper tooling is well below the lowest frequency measured, with these values, it is ensured that no resonant frequencies are picked up and the only frequencies picked up are those caused by a defect in the miniature bearing 19 which itself then causes radial movement with respect to its vertical axis when rotated by the rotor 5.

The signal picked up from the accelerometer 31 is transmitted to input 41, filtered, amplified and integrated by preamplifier and band pass filter 43 to obtain a velocity value. This signal is then passed onto RMS meter 45 to determine the RMS value thereof and thereafter amplified by audio amplifier 47 and transmitted through output 49 to a device which translates a signal into human perceptible form. In this regard, the output can be a speaker 51 or earphones 53. Alternatively, more sophisticated measurement and analytical techniques can be employed by transmitting the output at output 49 to either an oscilloscope 55 or a real time analyzer 57.

With respect to the electronic components employed, it is noted that, for example, the accelerometer preamplifier and band pass filter are conventional, typically commercially available from Trigtek of Annahein, Calif. The Accelerometer itself is also conventional in nature, for example, available from Endevco Company of California. The remaining components are also conventional and readily available as will be readily apparent to those of ordinary skill in the art.

What is claimed is:

1. A device for testing ball bearings and associated devices to detect flaws therein by detecting vibrations therefrom when in operation, the device comprising:
    a base;
    reed support means attached to said base and extending upwardly therefrom, said reed support means for supporting upper housing tooling;
    upper housing tooling mounted on said reed support means, said upper housing tooling having means for supporting a bearing thereon for rotational operation thereof and said reed support means, relative to said upper housing tooling, being flexible in a direction radial to the axis of rotation of a bearing mounted on said upper housing tooling;
    drive means for rotationally driving a bearing mounted on said upper housing tooling;
    detecting means connected to said reed support means for detecting movement of said reed support means in response to a bearing on said upper housing tooling being rotated, which movement is indicative of a defect in the bearing and is radial relative to the bearing being rotated.

2. A device as in claim 1 further comprising velocity detecting means for detecting the velocity of rotation at which a bearing is being rotated.

3. A device as in claim 1 wherein said drive means comprises a rotor body connectable to a bearing and configured for being driven in rotation by a pressurized air supply impinging thereon.

4. A device as in claim 2 wherein said velocity detecting means comprises a combination of a photocell and infrared LED positioned to have the radiation from the LED transmitted to said photocell and interrupted by predetermined portions of said rotor body upon rotation thereof to determine the speed of rotation of the rotor body as a function of photocell output.

5. A device as in claim 1 wherein said detecting means comprises an accelerometer connected to said reed support means to detect flexing thereof.

6. A device as in claim 5 wherein said reed support means is selected to have a length and thickness such that the resonant frequency of the reed support means with the upper housing tooling mounted thereon is at a value well below the lowest frequency measured by the accelerometer which lowest frequency measured is indicative of a flaw in a bearing being tested.

7. A device as in claim 6 wherein said accelerometer is connected to output electronics comprising; an accelerometer preamplifier for amplifying, filtering and integrating the output from the accelerometer to obtain a velocity signal indicative of movement of said reed support means; an RMS meter for receiving the velocity signal and determining the RMS value thereof; an amplifier for amplifying the resultant signal; and an output device for outputting a human perceptible representation of said signal.

8. A device as in claim 7 wherein said output device is a speaker.

9. A device as in claim 7 wherein said output device is a set of headphones.

10. A device as in claim 7 wherein said output device is an oscilloscope.

11. A device as in claim 7 wherein said output device is a real time analyzer.

12. A device as in claim 7 further comprising a band pass filter of the type which passes frequencies which are above 50 Hz, and wherein said accelerometer is of the type which is capable of measuring frequencies only as low as about 30 Hz.

* * * * *